US005304530A

United States Patent [19]

Cliff et al.

[11] Patent Number: 5,304,530
[45] Date of Patent: Apr. 19, 1994

[54] ACRYLATE FUNGICIDES

[75] Inventors: Geoffrey R. Cliff, Whittlesford; Ian C. Richards, Keddington, both of England

[73] Assignee: Schering Agrochemicals Limited, England

[21] Appl. No.: 5,284

[22] Filed: Jan. 19, 1993

Related U.S. Application Data

[62] Division of Ser. No. 216,831, Jul. 8, 1988, Pat. No. 5,192,357.

[30] Foreign Application Priority Data

Mar. 29, 1988 [GB] United Kingdom ............... 88/07388
Jul. 11, 1988 [GB] United Kingdom ............... 87/16392

[51] Int. Cl.[5] .................... A01N 43/00; A61K 31/425; C07D 265/30; C07D 277/62; C07D 333/02; C07D 317/00
[52] U.S. Cl. .................... 504/266; 504/224; 504/235; 504/246; 504/247; 504/262; 504/267; 504/270; 504/276; 504/293; 514/230.5; 514/239.2; 514/256; 514/306; 514/307; 514/311; 514/359; 514/362; 514/363; 514/365; 514/374; 514/381; 514/383; 514/385; 514/396; 514/406; 514/452; 514/464; 544/63; 544/158; 544/159; 544/180; 544/242; 546/174; 546/341; 548/127; 548/178; 548/146; 548/217; 548/255; 548/262.2; 548/267.8; 548/376.1; 548/342.1; 548/253; 548/325.1; 548/370.4; 548/307.1; 548/306.7; 549/29; 549/462

[58] Field of Search ............... 514/521, 525, 538, 539, 514/224.2, 222.5, 226.5, 238.5, 241, 256, 269, 311, 312, 359, 345, 357, 359, 362, 365, 366, 372, 375, 379, 380, 398, 399, 406, 438, 452, 230.5, 239.2, 306, 307, 362, 363, 365, 374, 381, 383, 385, 396, 406, 452, 464; 560/15, 16, 17, 19, 60; 562/426, 431, 440, 442, 470; 504/193, 235, 267, 246, 262, 267, 270, 272, 276, 277, 221, 282, 268, 224, 289, 226, 263, 247, 243, 254, 309, 295, 298, 296, 315, 293; 544/63, 180, 158, 159, 242; 546/174, 341; 548/127, 178, 217, 146, 217, 255, 262.2, 267.8, 341, 342, 253; 549/29, 162

[56] References Cited

U.S. PATENT DOCUMENTS 4,709,078 11/1987 Schirmer et al. ............... 560/60
4,723,034 2/1988 Schirmer et al. ............... 560/60
4,782,177 11/1988 Schirmer et al. ............... 560/60

*Primary Examiner*—José G. Dees
*Assistant Examiner*—Vera C. Clarke
*Attorney, Agent, or Firm*—Ostrolenk, Faber, Gerb & Soffen

[57] ABSTRACT

The invention provides compounds of formula I

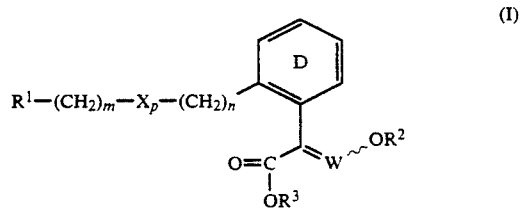

wherein W, D, $R^1$, $R^2$, $R^3$, X, m, n and p are as defined in the description. The compound have valuable pesticidal activity especially against fungi, insects, nematodes, acarids and weeds.

16 Claims, No Drawings

ACRYLATE FUNGICIDES

This is a division of application Ser. No. 07/216,831, filed Jul. 8, 1988 and now U.S. Pat. No. 5,192,357.

This invention relates to compounds having fungicidal, insecticidal, ectoparasiticidal or herbicidal activity.

Derivatives of acrylic acid having fungicidal activity have recently been described in a number of publications, and especially EP 178826 and 203608.

According to the invention there is provided a compound of formula I

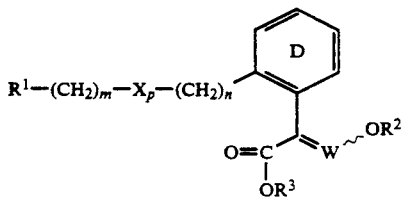

wherein either
A) W is CQ, in which either
 a) Q is hydrogen, $R^3$ is hydrogen or alkyl, p is 1 and
  (i) n is 1, m is 0, X is S, O, SO, $SO_2$, $NR^4$, Si($OR^2$)$R^2$, Si($R^2$)$_2$ or Si($OR^2$)$_2$ and $R^1$ is $R^5$, where $R^5$ is optionally substituted heteroaryl, optionally substituted heterocyclyl, optionally substituted heterocyclyl(thio)carbonyl, optionally substituted alkenyl, optionally substituted alkynyl, optionally substituted N-substituted iminomethylene, substituted heterocyclylidenemethyl; or
  (ii) n is 0, m is 1 to 18, X is S and $R^1$ is $R^5$ or is optionally substituted aryl; or
 b) Q and $R^3$ form part of a five or six membered ring which may be substituted and can contain other hetero atoms, especially nitrogen, p is 0 or 1, m and n are 0 to 18, at least one of m, n and p being greater than 0; X is S, O, SO, $SO_2$, $NR^2$, Si($OR^2$)$R^2$, Si($R^2$)$_2$ or Si($OR^2$)$_2$ and $R^1$ is $R^5$ or is hydrogen, optionally substituted alkyl or optionally substituted aryl; or
B) W is N, in which case $R^3$ is hydrogen or alkyl, m is 0, p and n are 1, X is O, S, $NR^2$, Si($OR^2$)$R^2$, Si($R^2$)$_2$ or Si($OR^2$)$_2$ and $R^1$ is $R^5$;
$R^2$ is alkyl;
$R^4$ is alkyl or is a bond linked to $R^1$ and the ring D is optionally substituted; and acid addition salts of any compounds which are basic and basic addition salts of any compounds which are acidic.

Compounds of the invention exist as structural isomers and the invention includes individual isomers as well as mixtures of these.

Alkyl groups are preferably of 1 to 4 carbon atoms, especially methyl or ethyl. Alkenyl and alkynyl groups are generally of three to six carbon atoms. Substituents, when present on any alkyl, alkenyl or alkynyl group, include halogen, alkoxy (e.g. of 1 to 4 carbon atoms), haloalkoxy (e.g. difluoromethoxy) hydroxy, alkylthio, nitro, optionally substituted amino, carboxy, alkoxycarbonyl, cyano, acyloxy and aryl. Aryl groups are usually phenyl, optionally substituted, e.g. by halogen, optionally substituted alkyl or alkoxy, aryl, aryloxy, nitro, amino, COOH, $COOR^2$, CN, $CONR^2R^2$ or $S(O)_nR^2$.

The terms heteroaryl and heterocyclyl include groups such as thienyl, furyl, pyridyl, pyrimidinyl, pyrazolyl, thiazolyl, thiazolinyl, thiazolone, oxazolyl, benzimidazolyl, tetrazolyl, benzoxazolyl, thiadiazolyl, dioxolanyl, imidazopyridinyl, 1,3-benzoxazinyl, 1,3-benzothiazinyl, oxazolopyridinyl, triazolyl, triazinyl, imidazolyl, morpholino, benzofuranyl, pyrazolinyl, guinolinyl, quinazolinyl, dihydroguinazolinyl or benzothiazolyl, which themselves may be substituted, e.g. as for phenyl. The ring D can be substituted in a similar manner as described for phenyl as well as by carboxy, alkoxycarbonyl, sulphonyl and sulphonamido groups. The term 'acyl' includes the residue of sulphonic and phosphorus containing acids as well as carboxylic acids. Acyl groups are preferably alkanoyl e.g. of 1 to 4 carbon atoms. Amino groups may be substituted. e.g. by one or two alkyl groups or two substituents can form a ring, e.g. to form a morpholino or piperidino ring. Iminomethylene groups can be sustituted both on the nitrogen and carbon. Examples of substituents on the nitrogen include aryl and alkyl. Examples of substiuents on the carbon include aryl, alkyl, alkylthio, alkoxy and cyano.

A particularly preferred group of compounds are those where n is 1, p is 1, m is 0, W is CH or N, $R^2$ and $R^3$ are methyl, X is S and $R^1$ is heteroaryl.

The compounds of the invention are particularly valuable as fungicides, especially against fungal diseases of plants, e.g. mildews and particularly cereal powdery mildew (*Erysiphe graminis*), vine downy mildew (*Plasmopara viticola*), rice blast (*Pyricularia oryzae*), cereal eyespot (*Pseudocercosporella herpotrichoides*), rice sheath blight (*Pellicularia sasakii*), grey mould (*Botrytis cinerea*), damping off (*Rhizoctonia solani*), wheat brown rust (*Puccinia recondita*), potato blight (*Phytophthora infestans*) and apple scab (*Venturia inaequalis*). Other fungi against which the compounds may be active include other powdery mildews, other rusts, and general pathogens of Deuteromycete, Ascomycete, Phycomycete and Basidomycete origin.

The compounds of the invention also have insecticidal, acaricidal and nematicidal activity and are particularly useful in combating a variety of economically important insects, acarids and plant nematodes, including animal ectoparasites and especially Diptera, such as sheep blow-fly, *Lucilia sericata,* and house-flies, *Musca domestica;* Lepidoptera, including *Plutella xylostella, Spodoptera littoralis, Heliothis armigera* and *Pieris brassicae;* Homoptera, including aphids such as *Megoura viciae;* Coleoptera, including corn rootworms (Diabrotica spp., e.g. *Diabrotioa undecimpunctata*); and spider mites, such as Tetranychus spp..

They may also have herbicidal activity.

The invention thus also provides a method of combating pests (i.e. fungi, insects, nematodes, acarids and weeds) at a locus infested or liable to be infested therewith, which comprises applying to the locus a compound of formula I.

The invention also provides an agricultural composition comprising a compound of formula I in admixture with an agriculturally acceptable diluent or carrier.

The composition of the invention may of course include more than one compound of the invention.

In addition the composition can comprise one or more additional active ingredients, for example compounds known to possess plant-growth regulant, herbicidal, fungicidal, insecticidal or acaricidal properties.

Alternatively the compounds of the invention can be used in sequence with the other active ingredient.

The diluent or carrier in the composition of the invention can be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or salts of such esters; fatty alcohol sulphates such as sodium dodecyl sulphate, sodium octadeoyl sulphate or sodium cetyl sulphate; ethoxylated fatty alcohol sulphates; ethoxylated alkylphenol sulphates; lignin sulphonates; petroleum sulphonates; alkyl-aryl sulphonates such as alkyl-benzene sulphonates or lower alkyl-naphthalene sulphonates, e.g. butyl-naphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine or the dialkyl sulphosuccinates, e.g. the sodium sulphonate of dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols.

Examples of a cationic surface-active agent include, for instance, an aliphatic mono-, di-, or polyamine as an acetate, naphthenate or oleate; an oxygen-containing amine such as an amine oxide or polyoxyethylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution, a dispersion, an aqueous emulsion, a dusting powder, a seed dressing, a fumigant, a smoke, a bait, a dispersible powder, an emulsifiable concentrate or granules. Moreover it can be in a suitable form for direct application or as a concentrate or primary composition which requires dilution with a suitable quantity of water or other diluent before application.

An emulsifiable concentrate comprises a compound of the invention dissolved in a water-immiscible solvent which is formed into an emulsion with water in the presence of an emulsifying agent.

A dusting powder comprises a compound of the invention intimately mixed and ground with a solid pulverulent diluent, for example, kaolin.

A granular solid comprises a compound of the invention associated with similar diluents to those which may be employed in dusting powders, but the mixture is granulated by known methods. Alternatively it comprises the active ingredient absorbed or adsorbed on a pre-granular diluent, for example, Fuller's earth, attapulgite or limestone grit.

Wettable powders, granules or grains usually comprise the active ingredient in admixture with a suitable surfactant and an inert powder diluent such as china clay.

Another suitable concentrate is a flowable suspension concentrate which is formed by grinding the compound with water or other liquid, a wetting agent and a suspending agent.

The concentration of the active ingredient in the composition of the present invention, as applied to plants is preferably within the range of 0.001 to 3.0 per cent by weight, especially 0.01 to 1.0 per cent by weight. In a primary composition the amount of active ingredient can vary widely and can be, for example, from 5 to 95 per cent by weight of the composition.

In the method of the invention the compound is generally applied to seeds, plants or their habitat. Thus the compound can be applied directly to the soil before, at or after drilling so that the presence of active compound in the soil can control the growth of fungi which may attack seeds. When the soil is treated directly the active compound can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 0.05 to 20 kg per hectare, more preferably from 0.1 to 10 kg per hectare.

Alternatively the active compound can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control of fungi in the early stages of plant growth as this is the time when the plant can be most severely damaged. The spray or dust can conveniently contain a pre- or post-emergence herbicide if this is thought necessary. Sometimes, it is practicable to treat the roots of a plant before or during planting, for example, by dipping the roots in a suitable liquid or solid composition. When the active compound is applied directly to the plant a suitable rate of application is from 0.01 to 10 kg. per hectare, preferably from 0.05 to 5 kg per hectare.

The compounds of the invention may be prepared in a variety of ways. e.g. by reacting a compound of formula II

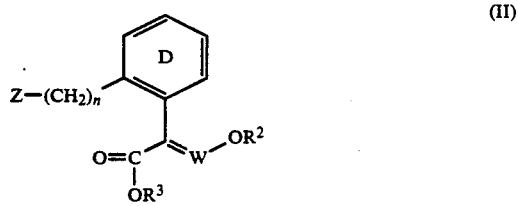

(II)

wherein Z is a leaving group, such as halogen, with a compound of formula III

(III)

Alternatively when W is CH. a compound of formula IV

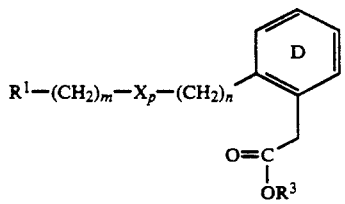

(IV)

can be reacted with a formate ester of formula V

HCOOR² (V)

under basic conditions.

Compounds where X is SO or $SO_2$ can be obtained by oxidising a compound where X is S, with a suitable oxidising agent such as meta-chloroperbenzoic acid. Other methods will be apparent to the chemist skilled in the art as will be the methods for preparing starting materials and intermediates. The Examples also make apparent various methods of preparing compounds of the invention as well as starting materials and intermediates The invention is illustrated in the following examples. Structures of isolated novel compounds were confirmed by elemental and/or other appropriate analyses. Temperatures are in °C.

EXAMPLE 1

Methyl o-tolylacetate (100 g) was dissolved in a mixture of methyl formate (450 ml) and dimethyl formamide 200 ml). The solution was added to a petrol washed suspension of sodium hydride (from 36 5 g of an 80% dispersion in oil) in dimethylformamide (100 ml) with cooling. The mixture was then stirred at room temperature overnight. Excess methyl formate and most of the dimethylformamide were evaporated and water (500 ml) was added. The mixture was treated with ether and the aqueous phase separated, acidified and extracted with ether. The extract was worked up in conventional manner to give a brown oil. This was dissolved in tetrahydrofuran and the solution added dropwise to sodium hydride (16.5 g of 80% dispersion in oil) in tetrahydrofuran (50 ml) with cooling. When no more hydrogen had evolved, methyl iodide (35 ml) was added and the mixture heated to reflux for 5 hours. Methanol (5 ml) was added and the solvent evaporated. The resulting oil was Partitioned between ether and water and the organic phase worked up in conventional manner to give to give methyl (Z)-3-methoxy-2-(o-tolyl)prop-2-enoate, m.p. 68°-70°. This product (185 g) was dissolved in carbon tetrachloride (1250 ml). N-Bromosuccinimide (159.3 g) was added and the mixture heated under reflux for 3 hours. The reaction mixture was then cooled and worked up to give a light brown oil. The crude product was triturated with a 10% solution of di-isopropyl ether in light Petroleum to give methyl (E)-3-methoxy-2-[(2-bromomethyl)phenyl]-prop-2-enoate, m.p. 87°-90° C. 2-Mercaptobenzo-thiazole (101.87 g) in tetrahydrofuran (600 ml) was added dropwise with stirring to a petrol washed suspension of sodium hydride (from 18.42 g of 80% dispersion in oil), in tetrahydrofuran 200 ml). The mixture was heated under reflux for 30 minutes and cooled to room temperature. A solution of the bromomethyl compound (175 g) in tetrahydrofuran (1000 ml) was added over one hour and the mixture stirred for 5 hours at room temperature. Aqueous tetrahydrofuran was added to quench the reaction and the mixture was evaporated. The residue was worked up in conventional manner to give methyl (E)-2-[2-[[(2-benzothiazolyl)thio]methyl]-phenyl]-3-methoxy-2-propenoate, m.p. 77°-78°. (Compound 1)

EXAMPLE 2

Potassium carbonate (25 g) was added to a stirred solution of o-tolylacetic acid (7.5 g) in acetonitrile (125 ml). The mixture was stirred for ten minutes at room temperature. Ethyl chloroacetate (6.13 g) was added and the mixture heated at reflux overnight. It was then poured into water, acidified with concentrated hydrochloric acid to pH2 and extracted with ethyl acetate. The extract was washed with brine, dried and evaporated, and purified by column chromatography to give ethoxycarbonylmethyl o-tolylacetate. Potassium carbonate 15 g) was added to a stirred solution of this product (10 g) in dimethylformamide (100 ml). The mixture was stirred at room temperature for 72 hours and then heated at reflux overnight. The mixture was cooled to 0° C. and potassium carbonate (5 g) added, followed by methyl iodide (2.65 ml). The mixture was stirred at room temperature for 24 hours. The mixture was poured into water, extracted with ether and the extract washed with brine, dried and evaporated to give 3-(2-methylphenyl)-4-methoxyfuran-2(5H)-one, as a gum. This was then treated with N-bromosuccinimide followed by reaction with 2-mecaptobenzothiazole, in a similar manner to that described in Example 1, to give 3-[2-[[(2-benzothiazolyl)thio]methyl]phenyl]-4-methoxyfuran-2(5H)-one m.p. 81°-82°. (Compound 2)

EXAMPLE 3

Benzo[b]thiophen-2(3H)-one (6g) and sodium hydroxide (3.2 g) were refluxed in water (40 ml) for one hour. 4-Chlorobenzyl chloride (6.44 g was added and the mixture refluxed for a further 1½ hours and allowed to cool overnight. Water (25 ml) was added, followed by acetic acid (100 ml). The solid was collected, washed with water and dried to give [2-(4-chlorobenzylthio)-phenyl]acetic acid, m.p. 149°-51°. A solution of this product 10.4 g) in methanol (250 ml) containing concentrated sulphuric acid (0.5 ml) was heated under reflux overnight and excess methanol evaporated. Ether and water were added and the organic phase was washed with aqueous sodium hydroxide, dried and evaporated. The product which solidified was re-crystallised from hexane to give the methyl ester of the starting acid, m.p. 52°-4°. This was treated with methyl formate and sodium hydride in a similar manner to the procedure described in Example 1 to give methyl (E)-3-methoxy-2-[2-(4-chlorobenzylthio)phenyl]prop-2-enoate, m.p. 81°-4°, (Compound 3) and the corresponding Z-isomer, m.p. 127°-8°. (Compound 4), which were separated by silica gel column chromatography.

EXAMPLE 4

Methyl chlorooxoacetate (22.5 ml) in tetrahydrofuran (60 ml) was added, dropwise, over one hour to a stirred solution of imidazole (33.35 g) in tetrahydrofuran (500 ml) maintained at 0°, under nitrogen. The mixture was then stirred for a further hour at this temperature. The reaction mixture was filtered and the precipitate washed with tetrahydrofuran. The filtrate and washings, containing methyl α-oxo-1H-imidazole- 1-acetate, were cooled to −65° C. and a solution of a Grignard reagent, prepared from o-bromotoluene (42 g), 1,2-dibromoethane 3.6 ml) and magnesium (7 g), in tetrahydrofuran, was added over 45 minutes, whilst maintaining the temperature at between −60 to −70°. The mixture was then stirred at this temperature for 15 minutes and at room temperature for 2½ hours. It was then poured into ice/water, extracted with ether, the extracts washed with brine, dried and concentrated. The residue was distilled under reduced pressure to give methyl oxo(o-tolyl)acetate, b.p. 92°–97°/0.5 mm. A solution of this product (5 g) in methanol (100 ml) was heated under reflux for 3 hours with methoxyamine hydrochloride (2.55 g). The mixture was cooled, evaporated, triturated with diisopropyl ether, filtered and the filtrate evaporated to give methyl (methoxyimino)(o-tolyl)acetate. This was then treated with N-bromosuccinimide in carbon tetrachloride at reflux under a 300 watt lamp with the addition of benzoyl peroxide (0.005 g every 10 minutes. Conventional work up gave the bromomethyl compound which was then reacted with 2-mercaptobenzothiazole, in a similar manner to that described in Example 1, to give methyl [2-[[(2-benzothiazolyl)thio]methyl]phenyl](methoxyimino)acetate, m.p. 113°–4°. (Compound 5)

In a similar manner to that described in one of the previous examples, the following compounds were obtained: Unless otherwise stated the compounds are in the E-form.

$R^1-(CH_2)_m-X_p-(CH_2)_n$-

MeOCO  CH—OMe

| Cpd no. | $R^1$ | $X_p$ | m | n | m.p. |
|---|---|---|---|---|---|
| 6 | 6-EtO-benzothiazol-2-yl | S | 0 | 1 | 100–101 |
| 7 | benzoxazol-2-yl | S | 0 | 1 | oil |
| 8 | 1-Me-imidazol-2-yl | S | 0 | 1 | 102–104 |
| 9 | 4-Me-pyrimidin-2-yl | S | 0 | 1 | 94–95 |
| 10 | 4,6-Me$_2$-pyrimidin-2-yl | S | 0 | 1 | oil |
| 11 | 4-Bu$^t$-1H-imidazol-2-yl | S | 0 | 1 | glass |
| 12 | (MeS)(3-Me-5-oxo-1-Ph-pyrazolin-4-ylidine)methyl | S | 0 | 1 | 129–131 |
| 13 | pyrimidin-2-yl | S | 0 | 1 | 75–76 |
| 14 | 2-thiazolin-2-yl | S | 0 | 1 | 105–106 |
| 15 | 5-MeCO-benzothiazol-2-yl | S | 0 | 1 | 109–110 |
| 16 | Ph (Z-isomer) | S | 1 | 0 | 92–4 |
| 17 | 5-CF$_3$-benzimidazol-2-yl | S | 0 | 1 | oil |
| 18 | 1-Ph-tetrazol-5-yl | S | 0 | 1 | 126–127 |
| 19 | 5-CF$_3$-benzothiazol-2-yl | S | 0 | 1 | 97–99 |
| 20 | Ph | S | 1 | 0 | 71–74 |
| 21 | 4,4-Me$_2$-5-methylene-2-thiazolin-2-yl | S | 0 | 1 | 101 |
| 22 | 5-Ph-pyrimidin-2-yl | S | 0 | 1 | 105–106.5 |
| 23 | 6-Cl-4-Me-benzothiazol-2-yl | S | 0 | 1 | 89–91 |
| 24 | 5-Me-benzothiazol-2-yl | S | 0 | 1 | 83–85 |
| 25 | 5-aminobenzothiazol-2-yl | S | 0 | 1 | gum |
| 26 | 4-Cl-benzothiazol-2-yl | S | 0 | 1 | 152–154 |
| 27 | 2-pyridyl | S | 0 | 1 | 80–82 |
| 28 | 1-(3-NO$_2$-Ph)tetrazol-5-yl | S | 0 | 1 | 93–95 |
| 29 | 2-thienyl | S | 0 | 1 | 64–65 |
| 30 | 5-Me-benzoxazol-2-yl | S | 0 | 1 | 90–91 |
| 31 | 3-CN-4-COOEt-6-Me-2-pyridyl | S | 0 | 1 | 113–114 |
| 32 | 7-Cl-benzothiazol-2-yl | S | 0 | 1 | 132–134 |
| 33 | 5,6-Cl$_2$-1H-benzimidazol-2-yl | S | 0 | 1 | 169.5–171 |
| 34 | 5-Cl-benzoxazol-2-yl | S | 0 | 1 | 105–107 |
| 35 | 6-Cl-benzothiazol-2-yl | S | 0 | 1 | 110–112 |
| 36 | 1-MeS-2-CN-2-COOMe-vinyl | S | 0 | 1 | 85–85 |
| 37 | 5-(2-NO$_2$-benzylidene)-4-oxo-2-thiazolin-2-yl | S | 0 | 1 | 177–178.5 |

-continued

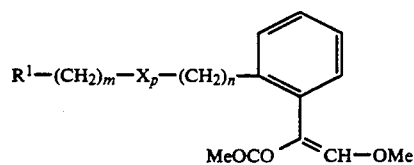

| Cpd no. | $R^1$ | $X_p$ | m | n | m.p. |
|---|---|---|---|---|---|
| 38 | 4-OH-5-Me-6-Pr-pyrimidin-2-yl | S | 0 | 1 | 169–170 |
| 39 | imidazo[1,5-a]pyridin-3-yl | S | 0 | 1 | 77–79 |
| 40 | 4-Ph-thiazol-2-yl | S | 0 | 1 | oil |
| 41 | 5-propargylthio-1,3,4-thiadiazol-2-yl | S | 0 | 1 | oil |
| 42 | 3-CN-4,6-Me$_2$-2-pyridyl | S | 0 | 1 | 140–142 |
| 43 | 3-MeO-Ph | S | 1 | 0 | 87–89 |
| 44 | 3-MeO-Ph (Z-isomer) | S | 1 | 0 | 95–97 |
| 45 | 1-Pr-benzimidazol-2-yl | S | 0 | 1 | 68–70 |
| 46 | 4-Bu$^t$-Ph | S | 1 | 0 | oil |
| 47 | 4-pyridyl | S | 0 | 1 | 101–103 |
| 48 | 1-benzylthio-2,2-diCN-vinyl | S | 0 | 1 | 97–98 |
| 49 | 1-Me-5-MeS-benzimidazol-2-yl | S | 0 | 1 | 90–92 |
| 50 | 1-Ph-1,2,4-triazol-3-yl | S | 0 | 1 | oil |
| 51 | 1-Pr$^i$-benzimidazol-2-yl | S | 0 | 1 | oil |
| 52 | 5-Br-benzothiazol-2-yl | S | 0 | 1 | 124–124.5 |
| 53 | 5-Br-1H-benzimidazol-2-yl | S | 0 | 1 | 179–180 |
| 54 | 2,2-Me$_2$-1,3-dioxolan-4-yl | S | 1 | 0 | oil |
| 55 | 2,2-Me$_2$-1,3-dioxolan-4-yl (Z-isomer) | S | 1 | 0 | oil |
| 56 | Ph | S | 2 | 0 | oil |
| 57 | Ph (Z-isomer) | S | 2 | 0 | oil |
| 58 | 7-Cl-4-MeO-benzothiazol-2-yl | S | 0 | 1 | gum |
| 59 | 1H-benzimidazol-2-yl | S | 0 | 1 | 166–168 |
| 60 | 5-Cl-benzothiazol-2-yl | S | 0 | 1 | 109–110 |
| 61 | 5-NO$_2$-benzoxazol-2-yl | S | 0 | 1 | 120–122 |
| 62 | 5-t-Bu-benzoxazol-2-yl | S | 0 | 1 | 85–87 |
| 63 | 5-EtS-1-Me-benzimidazol-2-yl | S | 0 | 1 | gum |
| 64 | 4,6,7-Cl$_3$-benzothiazol-2-yl | S | 0 | 1 | 159–161 |
| 65 | 5-Ph-thiazol-2-yl | S | 0 | 1 | oil |
| 66 | 5,7-Me$_2$-benzothiazol-2-yl | S | 0 | 1 | 97–98 |
| 67 | 6-Me-benzoxazol-2-yl | S | 0 | 1 | 70–73 |
| 68 | morpholinothioxomethyl | S | 0 | 1 | 97–99 |
| 69 | 4-Cl,3-MeO-Ph | S | 1 | 0 | oil |
| 70 | 1,2,4-triazol-1-yl | S | 1 | 0 | oil |
| 71 | 3-MeO-Ph | S | 2 | 0 | oil |
| 72 | 5,7-Cl$_2$-2,3-dihydrobenzofuran-2-yl | S | 1 | 0 | oil |
| 73 | Ph-CH=CH | S | 1 | 0 | oil |
| 74 | 1,2,4-triazin-3-yl | S | 0 | 1 | 163 |
| 75 | pyrimidin-4-yl | S | 0 | 1 | 101 |
| 76 | 2-Me-1,3-dioxolan-2-yl | S | 1 | 0 | oil |
| 77 | 6-Pr-benzothiazol-2-yl | S | 0 | 1 | oil |
| 78 | 6-PhO-benzothiazol-2-yl | S | 0 | 1 | 124–126 |
| 79 | 5-MeCONH-benzothiazol-2-yl | S | 0 | 1 | 151–153 |
| 80 | 4-Ph-Ph | S | 1 | 0 | 131–133 |
| 81 | Bu$^t$-C≡C | S | 2 | 0 | 76–77 |
| 82 | Bu$^t$-C≡C (Z-isomer) | S | 2 | 0 | oil |
| 83 | 4-(4-Cl-PhO)-Ph | S | 1 | 0 | 109–113 |
| 84 | 3-pyridyl | S | 1 | 0 | oil |
| 85 | 4-oxo-3,4-dihydropyrimidin-2-yl | S | 0 | 1 | 163 |
| 86 | 5-PhCONH-benzothiazol-2-yl | S | 0 | 1 | 100 |
| 87 | 5-(1,3-benzodioxol-5-yl-methyleneamino)benzothiazol-2-yl | S | 0 | 1 | foam |
| 88 | 4-oxo-3,4-dihydroquinazolin-2-yl | S | 0 | 1 | 223–226 |
| 89 | quinolin-2-yl | S | 0 | 1 | 88–90 |
| 90 | 3-Me-benzothiazol-2(3H)ylidine | N= | 0 | 1 | 139–141 |
| 91 | 4-(4-Cl-PhO)-Ph (Z-isomer) | S | 1 | 0 | 148–151 |
| 92 | 5-Ph-1,2,4-triazin-3-yl | S | 0 | 1 | 167 |
| 93 | 3-Ph-1,2,4-thiadiazol-5-yl | S | 0 | 1 | oil |
| 94 | 2-Ph-1,3-dioxolan-2-yl | S | 1 | 0 | oil |
| 95 | 2-Ph-1,3-dioxolan-2-yl (Z-isomer) | S | 1 | 0 | 120–122 |
| 96 | 5-PhCH=N-benzothiazol-2-yl | S | 0 | 1 | gum |
| 97 | 5-PhN=CH(MeS) | S | 0 | 1 | gum |
| 98 | 4-(4-Cl-Ph)-thiazol-2-yl | S | 0 | 1 | 99–102 |
| 99 | 4-(4-Me-Ph)-thiazol-2-yl | S | 0 | 1 | gum |
| 100 | 5-Me-4-Ph-thiazol-2-yl | S | 0 | 1 | 88–91 |

-continued

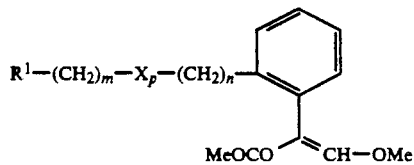

| Cpd no. | R¹ | $X_p$ | m | n | m.p. |
|---|---|---|---|---|---|
| 101 | 5-Cl-1-H-benzimidazol-2-yl | S | 0 | 1 | 161–164 |
| 102 | 3-Me-4-oxo-3,4-dihydro-quinazolin-2-yl | S | 0 | 1 | 144–146 |
| 103 | 4-Me-5-Ph-thiazol-2-yl | S | 0 | 1 | oil |
| 104 | 2H-1,4-benzothiazin-3-yl | S | 0 | 1 | oil |
| 105 | 2H-1,4-benzoxazin-3-yl | S | 0 | 1 | oil |
| 106 | 6-Cl-oxazolo[4,5-b]pyridin-2-yl | S | 0 | 1 | 114–116 |
| 107 | 5-Cl-1-Me-benzimidazol-2-yl | S | 0 | 1 | 132–135 |

In a similar manner to that described in Example 4, the following compounds were obtained:

$$R^1-(CH_2)_m-X_p-(CH_2)_n-\underset{MeOCO}{\underset{|}{C}}=N-OMe$$ (attached to phenyl)

| Cpd no. | R¹ | $X_p$ | m | n | m.p. |
|---|---|---|---|---|---|
| 108 | 5-Cl-benzothiazol-2-yl | S | 0 | 1 | 110–111 |
| 109 | benzoxazol-2-yl | S | 0 | 1 | 111–113 |

There was also obtained in a similar manner to that described in Example 2, 4-methoxy-3-[2-(phenylthiomethyl)phenyl]furan-2(5H)-one. (Compound 110)

EXAMPLE 5

This example illustrates typical concentrates that can be formulated from compounds of the invention.

| a) Wettable powder | |
|---|---|
| Compound of the invention | 25% w/w |
| Sodium lignosulphonate | 5% w/w |
| Silica | 5% w/w |
| China clay | 65% w/w |
| b) Emulsifiable concentrate | |
| Compound of the invention | 250 g/l |
| Soprophor BSU¹ | 200 g/l |
| N-Methylpyrrolidone | 657 g/l |

¹Tristyrylphenolethoxylate nonionic emulsifier

TEST EXAMPLE A

Compounds are assessed for activity against one or more of the following:

a) Foliar Tests

*Phytophthora infestans*: late tomato blight (PI)
*Plasmopara viticola*: vine downy mildew (PV)
*Erysiphe graminis*: barley powdery mildew (EG)
*Pyricularia oryzae*: rice blast (PO)
*Pellicularia sasakii*: rice sheath blight (PS)
*Botrytis cinerea*: grey mould of tomato (BC)
*Venturia inaequalis*: apple scab (VI)
*Puccinia recondita*: brown wheat rust (PR)

Aqueous solutions or dispersions of the compounds at the desired concentration, including a wetting agent, were applied by spray or by drenching the stem base of the test plants. These plants were then inoculated with appropriate test pathogens and kept under controlled environment conditions suitable for maintaining plant growth and development of the disease. After an appropriate time, the degree of infection of the leaf surface was visually estimated.

Compounds were considered active if they gave greater than 50% control of the disease at a concentration of 125 ppm (w/v) or less.

b) Soil Pathogen Test

In this tests compounds were assessed for activity against *Rhizoctonia solani* (RS).

Flasks containing maize meal/sand were inoculated with the test fungus and then incubated. The maize meal/sand cultures were used to infest potting compost which was then put into plastic pots. Aqueous solutions or dispersions of the compounds, including a wetting agent, were added to the pots to give a desired concentration of compound in each pot. Control pots were set up by adding similar solutions or dispersions without the test compound. Immediately after application of the test compound each pot was sown with a number of cabbage seeds. The seeds were covered with treated infested soil and the pots incubated under controlled environment conditions suitable for plant growth and development of the disease. The number of emerged cabbage seedlings is counted and percentage disease control calculated by comparison with the untreated infested pots.

Compounds were considered active if they gave greater than 50% control of the disease at a concentration of 100 parts by weight of compound or less per million parts by volume of soil.

Activities were demonstrated as follows (+ =active).

| Compound No | PI | PV | EG | PO | PS | BC | VI | RS | PR |
|---|---|---|---|---|---|---|---|---|---|
| 1 | + | + | + | + | | | + | | + |
| 2 | | + | | | | | | | |
| 3 | + | + | + | + | | | + | | + |
| 4 | | | | | | | + | | |
| 6 | + | | + | + | + | | | | + |
| 7 | + | | + | + | | | + | | + |
| 8 | | | | + | | | | | |
| 9 | + | + | + | + | | | + | | |
| 10 | | + | + | + | | + | + | | |
| 11 | | | | + | | | | | |
| 12 | + | | | + | | | | | |
| 13 | + | + | + | | | | + | | |
| 14 | + | + | + | | | | + | | |
| 15 | + | + | | + | | + | + | + | |
| 16 | + | + | | | | + | | | |
| 17 | | | | | | + | + | | |
| 18 | | | | | | | + | | |
| 19 | + | | + | + | | | + | | |
| 20 | + | + | | | | | + | | |
| 21 | + | | | | + | + | + | | + |
| 22 | + | + | + | + | + | + | + | | + |
| 23 | + | + | + | + | + | | + | | + |
| 24 | + | + | + | + | + | + | + | | + |
| 25 | + | + | + | + | + | | + | | |
| 26 | + | + | + | | | | + | | + |
| 27 | + | + | + | | | | + | + | |
| 28 | + | + | | | | + | | | |
| 29 | + | + | | | | | + | + | |
| 30 | + | + | + | | + | + | + | | + |
| 31 | + | + | | | | | + | + | |
| 32 | + | | + | + | | | + | | + |

-continued

| Compound No | PI | PV | EG | PO | PS | BC | VI | RS | PR |
|---|---|---|---|---|---|---|---|---|---|
| 33 | + | + | | | | | + | | |
| 34 | + | | + | + | + | | + | | + |
| 35 | + | | + | | | | + | | + |
| 36 | + | | | | | | + | | |
| 37 | | | + | | | | | | |
| 38 | | | | | | | + | | |
| 39 | | | | | | | + | | |
| 40 | + | | + | + | | | + | | + |
| 41 | | + | | | | | + | | |
| 42 | | + | + | | | | + | | + |
| 43 | + | + | + | | | | + | | |
| 44 | | | + | | | | + | | |
| 45 | + | | + | + | | | + | | |
| 46 | | | + | | | | + | | |
| 48 | | | | | | | + | | |
| 49 | + | + | + | + | + | + | + | | + |
| 50 | | + | + | | | | + | | |
| 51 | | + | + | | | | + | | |
| 52 | + | + | + | + | | | + | | + |
| 53 | | + | | | | | + | | |
| 56 | | + | | | | | + | | |
| 57 | | + | | | | | + | | |
| 59 | | + | | | | | + | | |
| 60 | + | | + | + | + | | + | | + |
| 61 | + | | | + | | + | | | |
| 62 | + | + | + | + | | | + | + | |
| 63 | + | | | | | | | | |
| 64 | + | | | | | | | | |
| 65 | + | | + | | | + | | | |
| 66 | + | | + | + | + | | + | | |
| 67 | + | | | + | | | + | | |
| 69 | | + | | | | | | | |
| 70 | | | | + | | | | | |
| 71 | | + | | | | | | | |
| 73 | | + | + | + | | | + | | |
| 74 | + | | | | | | | | |
| 75 | + | | | | | | + | | |
| 76 | + | + | + | + | + | | | | |
| 77 | + | + | + | | + | | + | | |
| 78 | + | + | + | | + | | + | | |
| 79 | + | + | | | | | | | |
| 80 | | + | | | + | | | | |
| 81 | | + | + | | | | + | | |
| 82 | | + | + | | | | + | | |
| 83 | | + | | | | | | | |
| 101 | | + | | + | | | | | |

TEST EXAMPLE B

This example illustrates the insecticidal activity of compounds of the invention.

1 ml Aliquots of an acetone solution containing test compound at various concentrations were applied to cotton wool dental rolls 1 cm×2 cm. contained in glass vials 2 cm diameter×5 cm long. After drying, the treated materials were then impregnated with 1 ml of nutrient solution, infested with first instar larvae of sheep blow fly (*Lucilia sericata*), closed by a cotton wool plug and held at 25° C. for 24 hours. For the controls the mortality was <5% whereas the compounds of Examples 6, 13, 15, 19, 21–24, 30, 32, 34, 35, 40, 49, 52, 60 and 61 had an $LC_{50}$ of less than 300 ppm.

We claim:
1. A compound of formula I

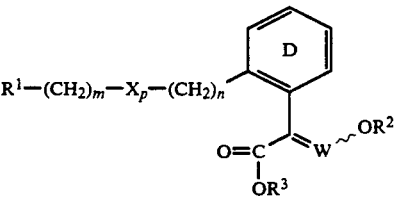

wherein either
A) W is CQ, in which either
  a) Q is hydrogen, $R^3$ is hydrogen or alkyl, p is 1 and
    (i) n is 1, m is 0, X is S, O, SO, $SO_2$, $NR^4$, Si-$(OR^2)R^2$, $Si(R^2)_2$ or $Si(OR^2)_2$ and $R^1$ is $R^5$, where $R^5$ is optionally substituted heteroaryl, optionally substituted heterocyclyl, optionally substituted heterocyclyl(thio)carbonyl, substituted heterocyclylidenemethyl; or
    (ii) n is 0, m is 1 to 18, X is S and $R^1$ is $R^5$ or is optionally substituted aryl; or
  b) Q and $R^3$ form part of a optionally substituted five or six membered ring p is 0 or 1, m and n are 0 to 18, at least one of m, n and P being greater than 0; X is S, O, SO, $SO_2$, $NR^2$, $Si(OR^2)R^2$, $Si(R^2)_2$ or $Si(OR^2)_2$ and $R^1$ is $R^5$ or is hydrogen, optionally substituted alkyl or optionally substituted aryl; or
B) W is N, in which case $R^3$ is hydrogen or alkyl, m is 0, p and n are 1, X is O, S, $NR^2$, $Si(OR^2)R^2$, $Si(R^2)_2$ or $Si(OR^2)_2$ and $R^1$ is $R^5$;
$R^2$ is alkyl;
$R^4$ is alkyl or is a bond linked to $R^1$ and the ring D is optionally substituted; and acid addition salts of any compounds which are basic and basic addition salts of any compounds which are acidic.

2. A compound according to claim 1 in which n is 1, p is 1, m is 0, W is CH or N, $R^2$ and $R^3$ are methyl, X is S and $R^1$ is heteroaryl.

3. An agricultural composition which comprises an effective amount of a compound claimed in claim 1 in admixture with an agriculturally acceptable diluent or carrier.

4. A method of combating insects. nematodes or acarids at a locus infested or liable to be infested therewith, which comprises applying to the locus an effective amount of a compound claimed in claim 1.

5. A method of combating fungi at a locus infested or liable to be infested therewith, which comprises applying to the locus an effective amount of a compound claimed in claim 1.

6. A method of combating weeds at a locus infested or liable to be infested therewith, which comprises applying to the locus an effective amount of a compound claimed in claim 1.

7. A compound according to claim 1 in which any heterocyclic moiety is selected from the group consisting of optionally substituted thiazole, thiazolinyl and thiazolone.

8. An agricultural composition which comprises an effective amount of a compound claimed in claim 7 in admixture with an agriculturally acceptable diluent or carrier.

9. A method of combating insects, nematodes or acarids at a locus infested or liable to be infested therewith, which comprises applying to the locus an effective amount of a compound claimed in claim 7.

10. A method of combating fungi at a locus infested or liable to be infested therewith, which comprises applying to the locus an effective amount of a compound claimed in claim 7.

11. A method of combating weeds at a locus infested or liable to be infested therewith, which comprises applying to the locus an effective amount of a compound claimed in claim 7.

12. An agricultural composition which comprises an effective amount of a compound claimed in claim 2 in admixture with an agriculturally acceptable diluent or carrier.

13. A method of combating insects, nematodes or acarids at a locus infested or liable to be infested therewith, which comprises applying to the locus an effective amount of a compound claimed in claim 2.

14. A method of combating fungi at a locus infested or liable to be infested therewith, which comprises applying to the locus an effective amount of a compound claimed in claim 2.

15. A method of combating weeds at a locus infested or liable to be infested therewith, which comprises applying to the locus an effective amount of a compound claimed in claim 2.

16. A compound according to claim 7 in which W is CH, $R^3$ is methyl, p is 1, n is 1, m is 0, X is S and $R^1$ is said heterocyclic moiety.

* * * * *

Adverse Decisions in Interference

Patent No. 5,304,530, Geoffrey R. Cliff, Ian C. Richards, ACRYLATE FUNGICIDES, Interference No. 103,905, final judgment adverse to the patentees rendered December 9, 1997, as to claims 1-16.
*(Official Gazette April 21, 1998)*